United States Patent [19]

Sayles

[11] 4,026,912

[45] May 31, 1977

[54] CARBORANYLDIFERROCENYLMETHYL PERCHLORATE

[75] Inventor: David C. Sayles, Huntsville, Ala.

[73] Assignee: The United States of America as represented by the Secretary of the Army, Washington, D.C.

[22] Filed: Mar. 3, 1971

[21] Appl. No.: 120,682

[52] U.S. Cl. .................. 260/439 CY; 149/19.9; 149/22; 149/75; 260/606.5 B

[51] Int. Cl.² ............... C07F 17/02; C07F 5/02

[58] Field of Search .......... 260/439 CY, 606.5 B; 149/22, 75, 109, 19.9

[56] References Cited

UNITED STATES PATENTS 3,789,609  2/1974  Hill .................. 149/19.2 X
3,860,463  1/1975  Sayler .................. 149/19.9

Primary Examiner—Edward A. Miller
Attorney, Agent, or Firm—Nathan Edelberg; Robert P. Gibson; Jack W. Voigt

[57] ABSTRACT

A mixed, intramolecular perchlorate salt, having a carboranyl moiety and two ferrocenyl moieties, is used as a partial replacement for ammonium perchlorate to achieve ultrahigh burning rates for propellants. The perchlorate salt when incorporated into a propellant composition contributes to the oxidizer function, and in addition, since both boron and iron are present, two mechanisms for burning rate catalysis are exploited. The described compound, carboranyldiferrocenylmethyl perchlorate, obviates the need for incorporating the burning rate catalysts separately.

1 Claim, No Drawings

CARBORANYLDIFERROCENYLMETHYL PERCHLORATE

DEDICATORY CLAUSE

The invention described herein may be manufactured, used, and licensed by or for the Government for governmental purposes without the payment to me of any royalties thereon.

BACKGROUND OF THE INVENTION

Both ferrocene and carborane and derivatives thereof have been used as burning rate catalysts. Normal-butylferrocene and normalhexylcarborane are typical ferrocene and carborane derivatives which have been used separately or in mixed catalyst systems for high burning rate propellants.

Various theories and proposed mechanism for propellant burning rates have evolved from experimentation in the field of catalysis. A rate controlling step for propellant burning rates is based on the rate of decomposition of ammonium perchlorate. Burning rates have been measured for propellants wherein the particle size of ammonium perchlorate has varied. The burning rates of propellants increase as the particle size of the ammonium perchlorate is decreased. Smaller particle sizes facilitate the decomposition rate of ammonium perchlorate.

Very fine particle-sized ammonium perchlorate (e.g. of only a few microns average mean weight diameter partical size) and catalysts, generally which have been incorporated in the propellant compositon as liquid plasticizers, have helped to achieve high burning rates for propellant composition. The use of the liquid-type catalysts has lead to other problems caused by catalyst-plasticizer migration into the liner-insulation system.

Desirable would be a catalyst which does not migrate after incorporation into propellant.

A highly effective catalyst to produce higher burning rates for a propellant composition is always desirable in that a small amount of catalyst can be used to change a propellant to yield the desired burning rates and ballistic properties.

A combination catalyst and oxidizer ingredient which can be used as a partial replacement for ammonium perchlorate without reducing the perchlorate ion content in the propellant would be even more highly desirable, especially if the catalyst-oxidezer ingredient is a solid ingredient and has excellent compatibility with the other propellant ingredients.

Therefore, an object of this invention is to provide a propellant ingredient which serves as a combined catalyst and oxidizer.

Another object of this invention is to provide a propellant ingredient which provides catalysis of the combustion process by at least two different reaction mechanisms.

A further object of this invention is to provide an oxidizer-catalyst ingredient which overcomes the problem of catalyst-plasticizer migration into the liner-insulation system.

Still a further object of this invention is to provide an oxidizer-catalyst ingredient which will permit the use of a lesser total amount of catalyst and ammonium perchlorate in a propellant formulation, and thereby permit the use of a larger quantity of binder, and/or fuel, and/or oxidizer in the formulation to yield a propellant of higher solids (metallic fuel, inorganic oxidizer) loading without adversely affecting the mechanical properties which is the situation which normally arises when the solids loading of a propellant is increased.

SUMMARY OF THE INVENTION

Carboranyldiferrocenylmethyl perchlorate serves as a partial replacement for the ammonium perchlorate oxidizer of a composite propellant composition to achieve higher burning rates than have been achievable by any other known technique in propellant.

The ferrocenyl and carboranyl functional groups are incorporated into the propellant formulation as part of the intramolecular structure of a solid salt. The solid salt is synthesized from decaborane by a series of reactions to yield carboranyldiferrocenylmethanol which is subsequently reacted with perchloric acid to form carboranyldiferrocenylmethyl perchlorate. The solid salt provides, in addition to oxidizer functions, catalytic functions by at least two different oxidation mechanisms near the decomposition site of the perchlorate radical which is the oxidizer moiety.

DESCRIPTION OF THE PREFERRED EMBODIMENT

The synthesis of carboranyldiferrocenylmethyl perchlorate can be accomplished by the following series of chemical steps, similar to the procedure described by A. N. Nesmeyanov, E. G. Perevalova, L. I. Leont'eva and Yu. A. Ustynyuk, Izvesta Akademii Nauk U.S.S.R., Scriya Khimcheskaya No. 3, pp 556–558, March 1966. It can be depicted by the following chemical equations:

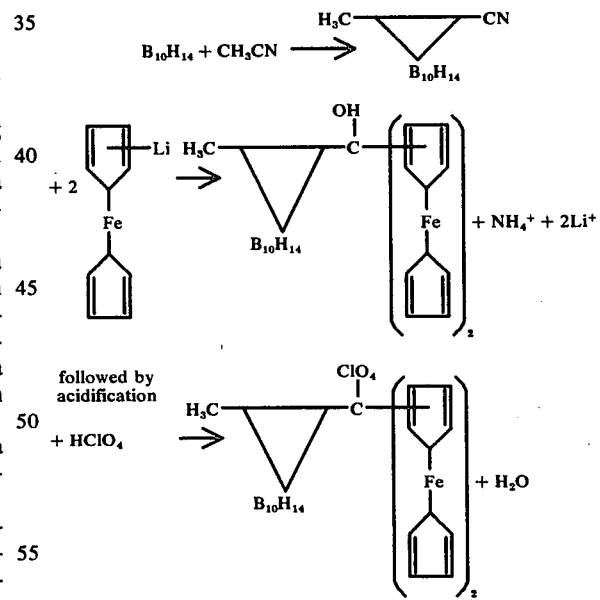

Carboranyl diferrocenylmethyl perchlorate

Synthesis of carboranyldiferrocenylmethyl perchlorate involves the following: Decaborane is converted into its acetonitrile adduct by reaction with acetonitrile. The carboranylcarbonitrile is reacted with ferrocenyllithium to form the carboranyldiferrocenylmethanol. The alcohol is reacted with perchloric acid to form the carboranyldiferrocenylmethyl perchlorate.

The use of carboranyldiferrocenylmethyl perchlorate in a composite propellant provides a means of introlucing a burning rate catalyst as part of a perchlorate oxidizer. Table I illustrates the use of the oxidizer-catalyst compound in an experimental composite propellant Composition B as compared with a standard high burning rate propellant Composition A.

The following advantages exist for propellants which contain this combined boron and iron catalyst:

a. catalyses of burning rate is controlled by two different combustion mechanisms to produce a higher burning rate than is obtained with the same percentages of current state-of-the-art burning rate catalysts.

b. Since the perchlorate radical of the intramolecular compound is available for use as oxidizer, less oxidizer ammonium perchlorate, AP) is needed; therefore, this permits the use of a larger amount of binder or inorganic oxidizer. If a larger quantity of the binder, such is, hydroxyl-terminated polybutadiene prepolymer, can be incorporated into a propellant, the resulting product would have improved mechanical properties and processing characteristics than otherwise.

c. If a lesser amount of binder is utilized than that set forth in composition B, additional aluminum and AP may be used to achieve a higher performance propellant.

d. Improved efficiency of catalyst utilization results from this combination since the burning rate catalyst is more intimately located at the potential decomposition site of the ammonium perchlorate. Decomposition of the ammonium perchlorate is the rate controlling step.

e. The problem of catalyst migration into the liner-insulation system is not encountered since the combined boron and iron catalyst is a solid salt.

specifically set forth in a commonly assigned Patent Application Serial No. 851,137, filed July 30, 1969. The nominal structure of the reaction product may be represented by the following general formula:

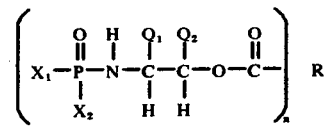

Where $X_1$ represents an aziridinyl group of the structure:

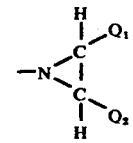

and $Q_1$ and $Q_2$ are either hydrogen or alkyl groups of one to four carbon atoms ($Q_1$ and $Q_2$ may be the same or different), $X_2$ may be the same as $X_1$ or may be an organic radical such as phenyl, benzyl, ethyl, etc., R is an alkyl that contains at least one active hydrogen atom or an organic entity of molecules that contain one or more hydroxyl groups, and $n$ is 2, 3, or 4.

The reaction product described above, is produced by dissolving the reactants in a suitable inert organic solvent such as methanol, ethanol, methylene chloride, tetrahydrofuran, diethyl ether, or mixtures of these. It

TABLE I
A COMPARISON OF PROPELLANTS CONTAINING CARBORANYL BURNING RATE PROMOTERS

| INGREDIENTS: | PROPELLANT A (STANDARD) WEIGHT PERCENT | PROPELLANT B (EXPERIMENTAL) WEIGHT PERCENT |
|---|---|---|
| Hydroxyl-terminated Polybutadiene-Based Prepolymer | 6.05 | 7.95 |
| Toluene diisocyanate | 0.50 | 0.50 |
| Bonding Agent | 0.35 | 0.35 |
| n-Hexylcarborane | 13.10 | — |
| Carboranyldiferrocenylmethyl perchlorate | — | 13.6 |
| Ammonium Perchlorate | 70.0 | 67.6 |
| Aluminum | 10.0 | 10.0 |
| BALLISTIC PROPERTIES: | | |
| Isps (1bf-sec/1bm) | 255 | 260 |
| Ispsd (in 6-in. diameter motors) (1bf-sec/1bm) | 245 | 250 |
| Pressure Exponent | 0.65 | 0.5–0.7 |
| Burning Rate (at 2000 psia) (ips) | 5.7 | 7.0 |
| MECHANICAL PROPERTIES: | | |
| Specific Weight (gm/cc) | 1.63 | 1.79 |
| Tensile Strength (psi) | 130 | 170 |
| Stress/Strain (psi/%) | | |
| −40° F | 330/30 | |
| +77° F | 150/60 | 250/100 |
| +140° F | 120/50 | |
| Elongation | 300 | 400 |

The bonding agent employed in the propellant compositions of Table I is added for the purpose of improving the mechanical properties of the cured propellant. The bonding agent functions as an interfacial bonding agent because it reacts with the ammonium perchlorate and the binder to form a chemical bond. When the propellant is then cured, a highly crosslinked network is produced among the AP, the binder and other propellant ingredients.

The interfacial bonding agents employed in the propellant formulations of this invention may be derived from di- or tri-functional aziridinylphosphine oxides or their derivatives with polyfunctional carboxylic acids as has been found to be preferable that methanol or ethanol comprise at least a part of the solvent. Reaction temperature is not critical, and may range from 70° F to 200° F for such time as is needed for essentially all carboxyl groups to be reacted. The solvent is then removed by any suitable means, such as evaporation under vacuum at elevated temperatures. The residue is the reaction product, an interfacial bonding agent, which is usually straw-colored and quite viscous.

The perchlorate salt of this invention may be used in a propellant composition in amounts from about 5 to about 20 weight percent of the propellant composition. The salt is easily blended, utilizing standard mixing equipment and procedures. OTher propellant ingredients include an additional oxidizer, preferably ammonium perchlorate, in amounts from about 60–72 weight percent, metal fuel (e.g. powdered aluminum, magnesium, titanium, zirconium, and boron) in amounts from about 5 to about 20 weight percent, a binder in amounts from about 6 to about 16 weight percent, a crosslinking agent in amounts from about 0.5 to about 1.0 weight percent, and additives for specific functions desired (e.g. ballistic modifiers, stabilizers, bonding agents etc.) in trace amounts from about 0.2 to 2.0 weight percent. Hydroxyl-terminated polybutadiene prepolymer serves as a binder after curing. The prepolymers are available with different functional groups and curatives or stabilizers. Appropriate crosslinking agents may be added. An appropriate crosslinking agent, toluene diisocyanate, is used with hydroxyl functional prepolymers to provide the necessary strength by crosslinking the binder for the propellant system. Additionally, the physical properties and stability of the propellant is enhanced by the use of from about 0.2 to about 0.4 weight percent of an interfacial bonding agent of the type described earlier herein.

The combination burning rate catalyst and oxidizer salt, carboranyldiferrocenylmethyl perchlorate, is compatible with a large number of propellant ingredients and can be advantageously utilized in propellant formulations which require higher burning rates than that which are presently derivable fom the available burning rate catalyst of the organometallic type. Carboranyldiferrocenylmethyl perchlorate is particularly suited for use with a propellant utilizing a high solids loading (e.g. high total percent of inorganic oxidizer, metal fuel, and a relatively small amount of a binder).

I claim:
1. The compound carboranyldiferrocenylmethyl perchlorate.

* * * * *